(12) United States Patent
Katayama

(10) Patent No.: US 9,031,199 B2
(45) Date of Patent: May 12, 2015

(54) X-RAY COMPUTED TOMOGRAPHY APPARATUS AND X-RAY DIAGNOSTIC APPARATUS

(75) Inventor: Shigeru Katayama, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 559 days.

(21) Appl. No.: 13/195,381

(22) Filed: Aug. 1, 2011

(65) Prior Publication Data

US 2012/0033783 A1 Feb. 9, 2012

(30) Foreign Application Priority Data

Aug. 5, 2010 (JP) ................................. 2010-176734

(51) Int. Cl.
| | |
|---|---|
| H05G 1/56 | (2006.01) |
| H05G 1/58 | (2006.01) |
| H05G 1/10 | (2006.01) |
| A61B 6/00 | (2006.01) |
| G06F 19/00 | (2011.01) |

(52) U.S. Cl.
CPC . *A61B 6/545* (2013.01); *A61B 6/00* (2013.01); *A61B 6/56* (2013.01); *G06F 19/30* (2013.01); *G06F 19/327* (2013.01); *G06F 19/3406* (2013.01); *Y10S 378/901* (2013.01)

(58) Field of Classification Search
USPC ......... 378/4–20, 91, 114, 117, 118, 162, 204, 378/210, 901; 250/370.01, 370.08, 370.09, 250/370.15, 371, 395, 493.1, 505.1, 526
See application file for complete search history.

(56) References Cited

U.S. PATENT DOCUMENTS 6,556,698 B1 * 4/2003 Diano et al. ................... 382/132
6,775,351 B2 * 8/2004 Rinaldi et al. ............... 378/98.8

(Continued)

FOREIGN PATENT DOCUMENTS

| CN | 101111782 A | 1/2008 |
|---|---|---|
| CN | 101146481 A | 3/2008 |

(Continued)

OTHER PUBLICATIONS

Combined Chinese Office Action and Search Report issued Apr. 9, 2013 in Patent Application No. 201110223272.4 with English Translation.

(Continued)

*Primary Examiner* — Anastasia Midkiff
(74) *Attorney, Agent, or Firm* — Oblon, Spivak, McClelland, Maier & Neustadt, L.L.P.

(57) ABSTRACT

According to one embodiment, in an X-ray computed tomography apparatus including a gantry unit including an X-ray tube and an X-ray detector, a bed unit, and a console, the X-ray computed tomography apparatus includes a storage unit, a power supply unit, and a power supply control unit. The storage unit stores examination schedule data of the X-ray computed tomography. The power supply unit selectively operates between an active mode of supplying power to at least one of the gantry unit, the bed unit, and the console and a standby mode of stopping supplying power to at least one of the bed unit and the gantry unit and supplying, to the console, power smaller than power supplied in the active mode. The power supply control unit controls switching from the active mode to the standby mode based on the examination schedule data.

11 Claims, 7 Drawing Sheets

(56) References Cited

U.S. PATENT DOCUMENTS

| | | | |
|---|---|---|---|
| 6,989,917 B2 * | 1/2006 | Honbo | 358/475 |
| 7,233,646 B2 | 6/2007 | Skaberna | |
| 2002/0015192 A1 | 2/2002 | Honbo | |
| 2004/0228452 A1 | 11/2004 | Rinaldi et al. | |
| 2006/0050849 A1 * | 3/2006 | Skaberna | 378/118 |
| 2006/0169907 A1 * | 8/2006 | Shinden | 250/370.09 |
| 2010/0074394 A1 * | 3/2010 | Nakamura et al. | 378/8 |

FOREIGN PATENT DOCUMENTS

| | | |
|---|---|---|
| CN | 101161203 A | 4/2008 |
| JP | 2001-178714 A | 7/2001 |
| JP | 2008-73121 A | 4/2008 |

OTHER PUBLICATIONS

Combined Chinese Office Action and Search Report issued Jan. 28, 2014, in Chinese Patent Application No. 201110223272.4 with English translation of category of cited documents.

Office Action mailed Dec. 16, 2014, in Chinese Patent Application No. 201310505109.6.

* cited by examiner

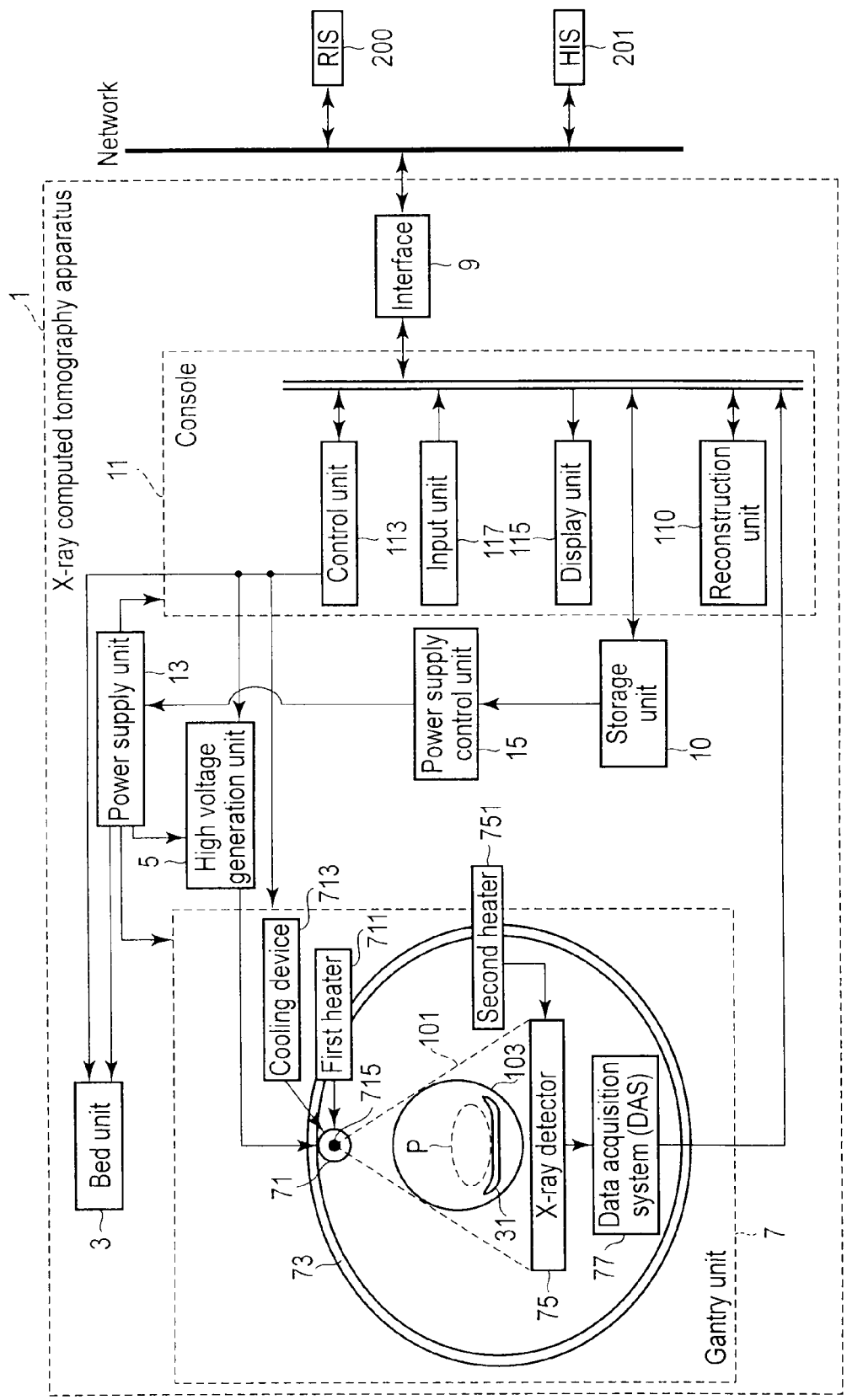
F I G. 1

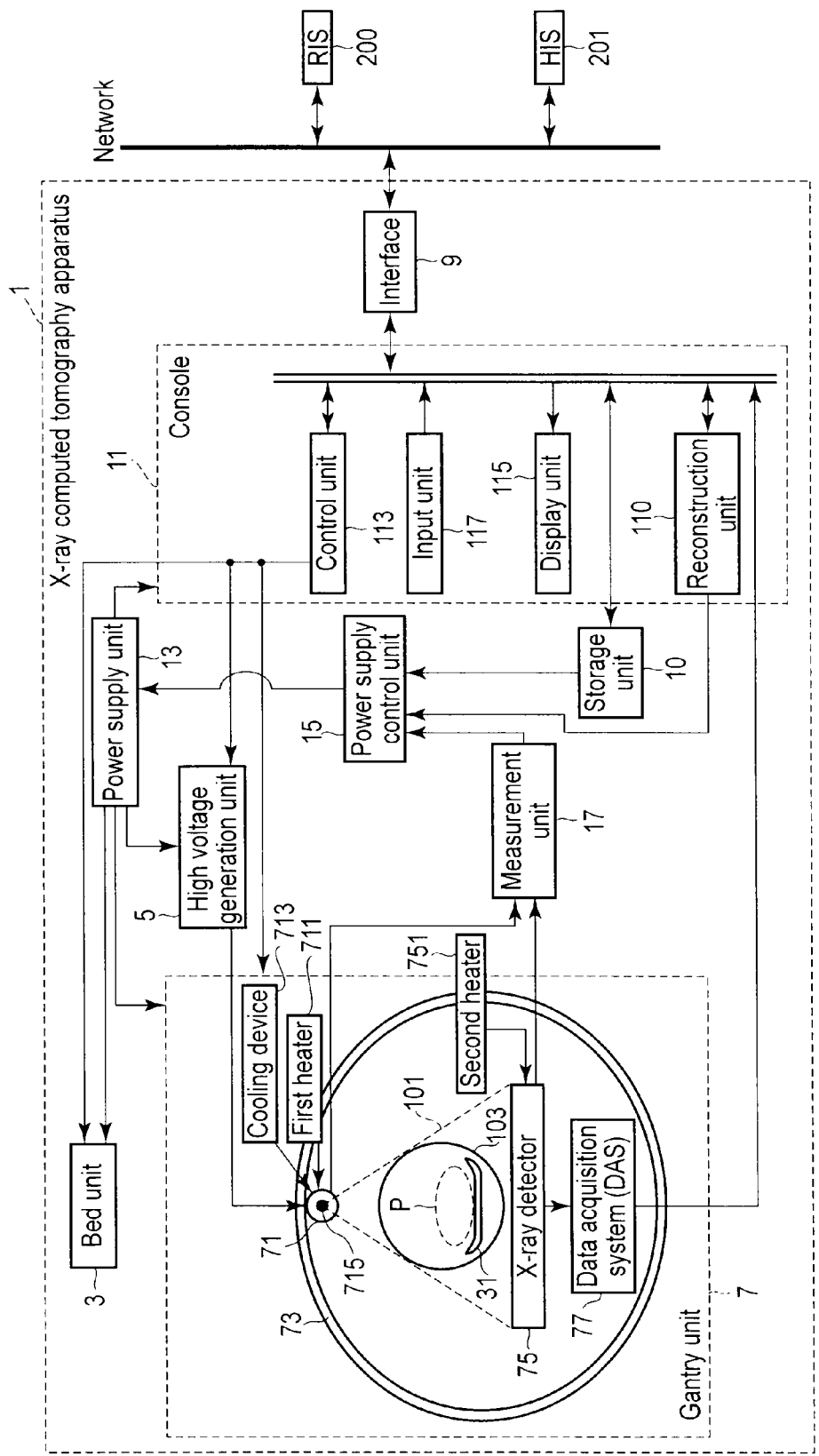
F I G. 4

US 9,031,199 B2

X-RAY COMPUTED TOMOGRAPHY APPARATUS AND X-RAY DIAGNOSTIC APPARATUS

CROSS-REFERENCE TO RELATED APPLICATIONS

This application is based upon and claims the benefit of priority from prior Japanese Patent Application No. 2010-176734, filed Aug. 5, 2010, the entire contents of which are incorporated herein by reference.

FIELD

Embodiments described herein relate generally to an X-ray computed tomography apparatus and an X-ray diagnostic apparatus.

BACKGROUND

Conventionally, an X-ray computed tomography apparatus and an X-ray diagnostic apparatus remain active as when they perform X-ray computed tomography and X-ray diagnosis, even in a standby mode during which they do not perform X-ray computed tomography and X-ray diagnosis, in order to accept urgent patients at any time (see FIG. 7). This poses a problem that the power consumption is large in the standby mode during which the apparatuses do not perform X-ray computed tomography and X-ray diagnosis.

BRIEF DESCRIPTION OF THE DRAWINGS

FIG. 1 is a view showing the arrangement of an X-ray computed tomography apparatus according to the first embodiment;

FIG. 4 is a view showing the arrangement of an X-ray computed tomography apparatus according to the second embodiment;

DETAILED DESCRIPTION

Figure 2:
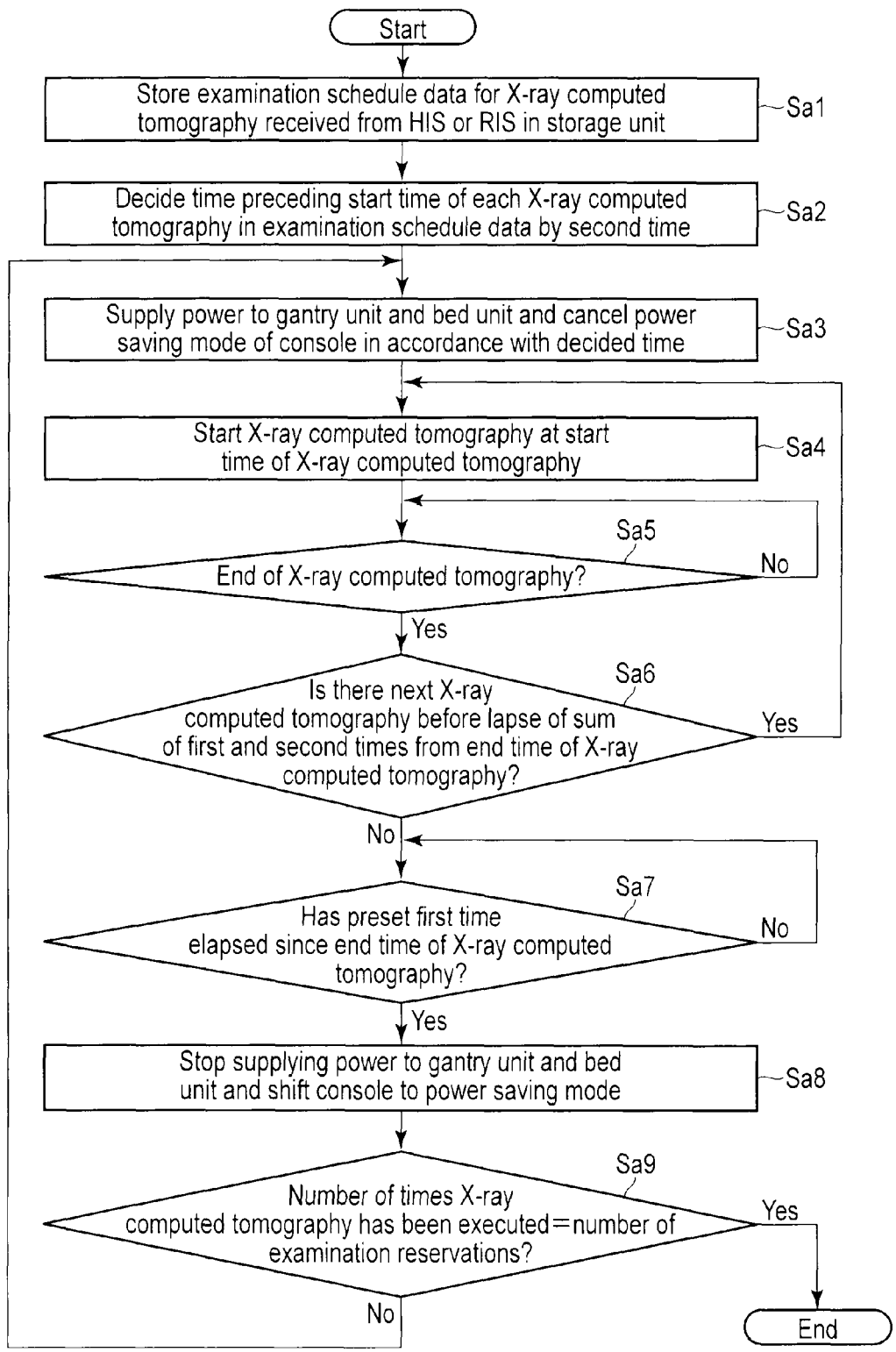
FIG. 2 is a flowchart showing a processing procedure for switching from the active mode to the standby mode and switching from the standby mode to the active mode based on examination schedule data of X-ray computed tomography according to the first embodiment.

In general, according to one embodiment, in an X-ray computed tomography apparatus including a gantry unit including an X-ray tube configured to generate X-rays and an X-ray detector configured to detect X-rays transmitted through an object, a bed unit on which the object is placed, and a console configured to control the gantry unit and the bed unit for X-ray computed tomography and reconstruct an image based on projection data acquired by X-ray computed tomography, the X-ray computed tomography apparatus includes a storage unit, a power supply unit, and a power supply control unit. The storage unit stores examination schedule data of the X-ray computed tomography. The power supply unit selectively operates between an active mode of supplying power to at least one of the gantry unit, the bed unit, and the console and a standby mode of stopping supplying power to at least one of the bed unit and the gantry unit and supplying, to the console, power smaller than power supplied in the active mode. The power supply control unit controls switching from the active mode to the standby mode based on the examination schedule data.

An embodiment of an X-ray computed tomography apparatus will be described below with reference to the accompanying drawing. Note that X-ray computed tomography apparatuses include various types of apparatuses such as a rotate/rotate-type apparatus in which an X-ray tube and an X-ray detector rotate together around an object, and a stationary/rotate-type apparatus in which many X-ray detection elements arrayed in the form of a ring are fixed, and only an X-ray tube rotates around an object. Either type can be applied to this embodiment. In order to reconstruct an image, projection data corresponding to one rotation around an object, i.e., 360°, is required, or (180°+fan angle) projection data is required in the half scan method. Either reconstruction scheme can be applied to the embodiment. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor such as selenium by X-rays and migration of the electron-hole pairs to an electrode, i.e., a photoconductive phenomenon. As an X-ray detection element, either of these schemes can be used.

Recently, with advances toward the commercialization of a so-called multi-tube type X-ray computed tomography apparatus having a plurality of pairs of X-ray tubes and X-ray detectors mounted on a rotating ring, related techniques have been developed. Both a conventional single-tube type X-ray computed tomography apparatus and a multi-tube type X-ray computed tomography apparatus can be applied to this embodiment. The single-tube type X-ray computed tomography apparatus will be exemplified here.

Note that the same reference numerals in the following description denote constituent elements having almost the same functions and arrangements, and a repetitive description will be made only when required.

(First Embodiment)

FIG. 1 is a view showing the arrangement of an X-ray computed tomography apparatus according to the first embodiment. An X-ray computed tomography apparatus 1 according to the first embodiment includes a bed unit 3, a high voltage generation unit 5, a gantry unit 7, an interface 9, a storage unit 10, a console 11, a power supply unit 13, and a power supply control unit 15.

The bed unit 3 includes a top 31 having an almost rectangular shape on which an object P is placed, a top support mechanism (not shown) which supports the top 31 so as to allow it to move individually in the longitudinal direction, the transverse direction, and the vertical direction, and a top control unit (not shown) which controls the top support mechanism. The top control unit controls the top support mechanism in accordance with an instruction from the operator in the active mode (to be described later). In the active mode, the bed unit 3 consumes a predetermined power to respond to an instruction from the operator even while no instruction is issued by the operator. In the standby mode (to be described later), since the power supply unit 13 (to be described later) stops supplying power to the bed unit 3, the bed unit 3 consumes no power. This saves the power consumed by the bed unit 3 as compared with the active mode.

The high voltage generation unit 5 includes a high voltage power supply (not shown) for applying a high voltage between the anode target and cathode filament of an X-ray tube 71 and a filament current generator (not shown) for supplying a filament current to the cathode filament of the X-ray tube 71. Note that the power supply unit 13 may supply power to the high voltage generation unit 5 in the active mode, and stops supplying power to the high voltage generation unit 5 in the standby mode. This saves the power consumed by the high voltage generation unit 5 as compared with the active mode.

The gantry unit 7 accommodates a rotating support mechanism. The rotating support mechanism includes a rotating ring 73, a ring support mechanism which supports the rotating ring 73 so as to allow it to rotate about a rotation axis Z, and a driving unit (electric motor) (not shown) which drives the rotation of the ring. The X-ray tube 71 and an area detector (to be referred to as an X-ray detector hereinafter) 75, which is also called a two-dimensional array type or multi-array type detector, are mounted on the rotating ring 73. A data acquisition circuit 77 called a DAS (Data Acquisition System) is connected to the output side of the X-ray detector 75. A first heater 711 and a cooling device 713 are connected to the X-ray tube 71. The first heater 711 preheats the X-ray tube 71 before the execution of X-ray computed tomography. The cooling device 713 suppresses heat load by the heat generated upon generation of X-rays. A second heater 751 is connected to the X-ray detector 75 to preheat it before the execution of an X-ray computed tomography.

The X-ray tube 71 receives a voltage and a filament current from the high voltage generation unit 5 via a slip ring (not shown) and generates X-rays from a focal point 715 of X-rays. A collimator unit (not shown) attached to the X-ray irradiation window of the X-ray tube 71 shapes the X-rays emerging from the focal point 715 of X-rays into, for example, a cone beam shape (pyramidal shape). The dotted line indicates an X-ray irradiation range 101. The X-axis is a straight line which is perpendicular to the rotation axis Z and passes through the focal point 715 of emitted X-rays. The Y-axis is a straight line perpendicular to the X-axis and the rotation axis Z. The X-ray tube 71 in this embodiment will be described as a rotating anode type X-ray tube. Note that other types of X-ray tubes such as a fixed anode type X-ray tube can be applied to this embodiment.

The X-ray tube 71 includes a cathode filament and a rotating anode target. The X-ray tube 71 mechanically supports a disk-like anode target by using a rotator and stator which have a bearing portion between them. The X-ray tube 71 rotates the disk-like anode target by supplying a rotary drive force to the electromagnetic coil of the stator placed at a position corresponding to the position of the rotator outside the vacuum vessel. The filament current generator of the high voltage generation unit 5 supplies a filament current to the cathode filament. The cathode filament is heated up to a predetermined temperature (to be referred to as the first threshold hereinafter) by a filament current. The heated cathode filament emits electrons. The emitted electrons collide with the anode target in accordance with the voltage applied from the high voltage power supply between the cathode filament and the anode filament. The electrons which have collided with the anode target emit X-rays. When the electrons collide with the anode target, the temperature of the anode target rises.

The X-ray tube 71 includes a tube protection function (OverLoad-Protection to be referred to as an OLP hereinafter) for preventing a failure in the X-ray tube 71 due to overload of heat accumulated by the generation of X-rays. The OLP has a function of inhibiting the heat accumulated in the X-ray tube 71 from exceeding a predetermined range, based on X-ray generation conditions (a tube voltage, tube current, and X-ray generation time), the time during which the generation of X-rays is stopped, the amount of heat generated by the X-ray tube 71, and the cooling efficiency of the cooling device 713 (to be described below).

The cooling device 713 includes a radiator and a pump (neither of which is shown). The cooling device 713 cools the X-ray tube 71. More specifically, the cooling device 713 cools the insulating oil filling the vessel main body of the X-ray tube 71. The insulating oil absorbs the heat generated by the anode target. The cooling device 713 cools the insulting oil in the X-ray tube 71 until the temperature of the X-ray tube 71 reaches a predetermined temperature (to be referred to as a predetermined threshold hereinafter). A state in which the temperature of the X-ray tube 71 has reached the predetermined threshold will be referred to as a cooled state hereinafter.

The first heater 711 is connected to the bearing portion of the X-ray tube 71. The first heater 711 heats the bearing portion up to a temperature (to be referred to as the second threshold hereinafter) equal to or more than the melting point of a liquid metal lubricant at the bearing portion before the rotation of the anode target of the X-ray tube 71. The bearing portion includes, for example, a rolling bearing such as a ball bearing or a dynamic pressure type sliding bearing using a liquid metal lubricant which becomes liquefied during rotation, such as gallium (Ga) or a gallium-indium-tin (Ga—In—Sn) alloy, on a bearing surface in which a helical groove is formed. Assume that in the following description, the bearing portion is formed from a dynamic pressure type sliding bearing.

The melting point of a liquid metal lubricant filling between the bearing surfaces of the dynamic pressure type sliding bearing is 10.7° C. when using, for example, a Ga—In—Sn alloy having a low melting point, and is 57° C. when using a Bi—In—Pb—Sn alloy containing bismuth (Bi). When the X-ray tube 71 is used in a temperature environment equal to or lower than the melting point of the liquid metal lubricant, the liquid metal lubricant is in a frozen state. For this reason, the first heater 711 heats the bearing portion to raise its temperature to the second threshold so as to melt the liquid metal lubricant before the start of the rotation of the anode target of the X-ray tube 71. If no liquid metal lubricant is used on the bearing portion of the X-ray tube 71 or the like, the first heater 711 may be omitted.

The X-ray detector 75 is mounted at a position and angle at which it faces the X-ray tube 71 through the rotation axis Z. The X-ray detector 75 includes a plurality of X-ray detection elements. Assume that in this case, each X-ray detection element forms a single channel. A plurality of channels are two-dimensionally arranged in two directions, i.e., the Z direction and a radial direction (channel direction) perpendicular to the rotation axis Z, with the focal point 715 of emitted X-rays being the center and the distance from the center to the center of the light-receiving portion of an X-ray detection element corresponding to one channel being a radius.

The X-ray detector 75 may be constituted by a plurality of modules each having X-ray detection elements arrayed in one line. Each module is one-dimensionally arrayed in an almost radial direction along the above channel direction. A plurality of X-ray detection elements may be two-dimensionally arrayed in two directions, i.e., the channel direction and the slice direction. That is, the two-dimensional arrangement is formed by arraying a plurality of channels, each arrayed one-dimensionally along the above channel direction, in the slice direction. The X-ray detector 75 having such a two-dimensional X-ray detection element arrangement may be formed by arraying the plurality of modules, each arrayed one-dimensionally in an almost radial direction, in a plurality of arrays in the slice direction.

The second heater 751 is connected to the X-ray detector 75. The second heater 751 heats the X-ray detector 75 to keep the X-ray sensitivity dependent on the temperature of the X-ray detection elements within a predetermined range. More specifically, when the temperature of the X-ray detector 75 becomes lower than the lower limit of a temperature range corresponding to the X-ray sensitivity in the predetermined range, the second heater 751 heats the X-ray detector 75 so as to prevent its temperature from exceeding the upper limit (to be referred to as the third threshold hereinafter) of the above temperature range. This makes the X-ray sensitivity of the X-ray detector 75 fall within the predetermined range.

A state in which the temperature of the bearing portion of the X-ray tube 71 has reached the second threshold, and the temperature of the X-ray detector 75 has reached the third threshold will be referred to as a heated state hereinafter. Note that the heated state may include a state in which the temperature of the cathode filament has reached the first threshold. The temperature states of the gantry unit 7 include two types of states, i.e., a cooled state and a heated state.

When performing imaging or scanning operation, the object P placed on the top 31 is inserted in a cylindrical imaging area 103 between the X-ray tube 71 and the X-ray detector 75. The data acquisition circuit 77 called a DAS is connected to the output side of the X-ray detector 75.

The data acquisition circuit 77 is attached with, for each channel, an I-V converter which converts a current signal for each channel of the X-ray detector 75 into a voltage, an integrator which periodically integrates the voltage signal in synchronism with an irradiation period of X-rays, an amplifier which amplifies an output signal from the integrator, and an analog/digital converter which converts an output signal from the amplifier into a digital signal. Data (to be referred to as pure raw data hereinafter) output from the data acquisition circuit 77 is transmitted to a preprocessing unit (not shown) via a noncontact data transmission unit (not shown) using magnetic transmission/reception or optical transmission/reception. The preprocessor preprocesses the pure raw data output from the data acquisition circuit 77.

Preprocessing includes, for example, sensitivity nonuniformity correction processing between channels and the processing of correcting an extreme decrease in signal intensity or signal omission due to an X-ray absorber, mainly a metal portion. The data (called raw data or projection data; projection data in this case) output from the preprocessor immediately before reconstruction processing is stored in the storage unit 10 including a magnetic disk, magneto-optical disk, or semiconductor memory in association with data representing view angles at the time of data acquisition. Note that projection data is a set of data values corresponding to the intensities of X-rays transmitted through the object. For the sake of descriptive convenience, a set of projection data which are almost simultaneously acquired by one shot throughout all the channels and have the same view angle will be referred to as a projection data set. The respective view angles are represented by angles in the range of 0° to 360° which represent the respective positions on a circular orbit centered on the rotation axis Z along which the X-ray tube 71 revolves, with the position of the uppermost position on the orbit in the vertically upward direction from the rotation axis Z being 0°. Projection data corresponding to each channel of a projection data set is identified by a view angle, a cone angle, and a channel number.

The interface 9 connects the console 11 to an electronic communication line (to be referred to as a network hereinafter). A radiology information system (to be referred to as an RIS hereinafter) 200 and a hospital information system (to be referred to as an HIS hereinafter) 201 are connected to the network.

The RIS 200 is a computer system for efficiently proceeding with tasks in the radiology department. More specifically, the RIS 200 is a computer system which performs reference to examination orders for the radiology department, recording of examination execution information, recording and transmission of accounting information, inventory management of consumable supplies such as films, and various kinds of statistic processes. A radiology technician or the like inputs the number of examination reservations for X-ray computed tomography to the RIS 200 based on a reservation table of examinations using the X-ray computed tomography apparatus. The HIS 201 is an overall computer system for efficiently performing tasks in the hospital. The HIS 201 includes a medical-affairs accounting system, an examination order system, a pharmaceutical system, a feeding system, and a ward management system. The RIS 200 issues an instruction document for X-ray computed tomography based on medical examination on a patient by a doctor. X-ray computed tomography is executed based on the issued instruction document for X-ray computed tomography.

The RIS 200 and the HIS 201 store examination schedule data of X-ray computed tomography including the start time data and end time data of X-ray computed tomography and the number of examination reservations. Examination schedule data includes the data input to the HIS 201 based on the interviews between doctors and patients and the data of the number of examination reservations input to the RIS 200 by a radiology technician and the like based on a reservation table of examinations by X-ray computed tomography. In the following description, for the sake of descriptive convenience, assume that the examination schedule data includes a plurality of number of times of X-ray computed tomography to be executed. That is, there are a plurality of examination reservations. Note that this embodiment can be applied to a case in which the examination schedule data includes only one X-ray computed tomography apparatus.

The storage unit 10 stores the images reconstructed by a reconstruction unit 110 of the console 11 (to be described below), the projection data output from the preprocessing unit, examination schedule data of X-ray computed tomography, the time (to be referred to as the first time hereinafter) taken for the temperature of the X-ray tube 71 to reach the cooled state from the end time of X-ray computed tomography, the time (to be referred to as the second time hereinafter) taken for the X-ray tube 71 to reach the heated state from the cooled state before the start time of X-ray computed tomography, control programs for controlling the bed unit 3, the high voltage generation unit 5, and the gantry unit 7 for X-ray computed tomography, and the like. Note that the storage unit 10 may be included in the console 11 (to be described below). It is possible to read out examination schedule data of X-ray computed tomography from a storage medium (not shown) via an interface or the like and store the data in the storage unit 10. It is also possible to receive examination schedule data of X-ray computed tomography from the RIS 200 or the HIS 201 via a network and the interface 9 and store the data in the storage unit 10.

Note that the operator may set at least one of the first and second times via the console 11. In addition, the operator can change at least one of the first and second times via the console 11. The second time may include the time (to be referred to as the third time hereinafter) taken for the cathode filament to reach the first threshold from the cooled state before the start time of X-ray computed tomography. The first time may be the time taken for the temperature of the X-ray tube 71 to reach a predetermined ratio relative to the OLP from the end time of X-ray computed tomography.

The console 11 includes the reconstruction unit 110, a control unit 113, a display unit 115, and an input unit 117. The reconstruction unit 110 reconstructs an image by using the projection data output from the preprocessing unit (not shown). The power supply unit 13 (to be described later) supplies power consumed by the console 11. Note that it is possible to supply power consumed by the console 11 via a local area network (to be referred to as a LAN hereinafter). The power supplied to the console 11 by the power supply unit 13 in the standby mode (to be described later) is smaller than that supplied to the console 11 by the power supply unit 13 in the active mode (to be described later). The state of the console 11 in the standby mode will be referred to as a power saving mode hereinafter. Each constituent element of the console 11 will be specifically described below.

The reconstruction unit 110 has a function of reconstructing a three-dimensional image in an almost columnar shape by the Feldkamp method or the cone beam reconstruction method based on a projection data set acquired in the view angle range of 360° or 180°+fan angle. An end area of volume data in a direction (Z direction) perpendicular to a slice surface includes an area in which 360° projection data for the reconstruction of a field of view area are not all prepared. The reliability of the volume data of an area lacking in projection data is low. The area lacking in projection data is not reconstructed or its reconstructed image is not displayed. This area is generally called a mask area.

The reconstruction unit 110 has a function of reconstructing two-dimensional images (tomograms) by, for example, the fan beam reconstruction method (also called the fan beam convolution back projection method) or the filtered back projection method. The Feldkamp method is a reconstruction method to be used when projection rays intersect a reconstruction plane like a cone beam. The Feldkamp method is an approximate reconstruction method, in which convolution processing is performed by regarding a cone beam as a fan projection beam on the premise that the cone angle is small, whereas back projection processing is performed along a ray in scanning operation. The cone beam reconstruction method is a reconstruction method which corrects projection data in accordance with the angle of a ray relative to a reconstruction plane as a method which suppresses cone angle errors more than the Feldkamp method.

The display unit 115 displays an image reconstructed by the reconstruction unit 110, an image stored in the storage unit 10, conditions set for X-ray computed tomography, and the like.

The input unit 117 inputs imaging conditions for X-ray computed tomography and the like which the operator desires. More specifically, the input unit 117 inputs various kinds of instructions, commands, information, choices, and settings from the operator to the X-ray computed tomography apparatus 1. Although not shown, the input unit 117 includes a trackball, switches, buttons, a mouse, and a keyboard for setting a region of interest and the like. The input unit 117 detects the coordinates of the cursor displayed on the display screen and outputs the detected coordinates to the control unit 113. Note that the input unit 117 may be a touch panel covering the display screen. In this case, the input unit 117 detects the coordinates indicated by a touch according to the coordinate reading principle based on an electromagnetic inductive, magnetostrictive, or pressure sensitive system, and outputs the detected coordinates to the control unit 113.

The control unit 113 functions as the main unit of the X-ray computed tomography apparatus 1. The control unit 113 includes a CPU and a memory (neither of which is shown). The control unit 113 controls the bed unit 3, the high voltage generation unit 5, and the gantry unit 7 for X-ray computed tomography based on the examination schedule data stored in the storage unit 10 and the control programs stored in the storage unit 10.

More specifically, the control unit 113 temporarily stores, in a memory (not shown), information such as an instruction from the operator and image processing conditions sent from the input unit 117. The control unit 113 controls the bed unit 3, the high voltage generation unit 5, and the gantry unit 7 based on these pieces of information temporarily stored in the memory. The control unit 113 reads out control programs for executing predetermined image generating/display operation and the like from the storage unit 10, and expands the programs in its own memory, thereby executing computation/processing and the like associated with various kinds of processing.

The power supply unit 13 supplies power to at least one of the bed unit 3, the high voltage generation unit 5, the gantry unit 7, and the console 11 under the control of the power supply control unit 15 (to be described later). The power supply unit 13 has the active mode of supplying power to at least one of the bed unit 3, the high voltage generation unit, the gantry unit 7, and the console 11 and the standby mode of stopping supplying power to at least one of the bed unit 3 and the gantry unit 7 and supplying, to the console 11, power smaller than that supplied in the active mode. The power supply unit 13 selects the active mode or the standby mode under the control of the power supply control unit 15. Note that the power supply unit 13 may supply power to the high voltage generation unit 5 in the standby mode. In the following description, for the sake of simplicity, assume that the power supply unit 13 supplies power to the bed unit 3, the high voltage generation unit 5, the gantry unit 7, and console 11 in the active mode. Assume also that the power supply unit 13 stops supplying power to the bed unit 3 and the gantry unit 7 in the standby mode.

The active mode is set in the time interval from the time (the time when the standby mode is switched to the active mode: to be referred to as the switching time to the active mode hereinafter) preceding the start time of X-ray computed tomography in examination schedule data by the second time to the time (the time when the active mode is switched to the standby mode: to be referred to as the switching time to the standby mode hereinafter) succeeding the end time of the X-ray computed tomography by the first time. The standby mode is set in the time interval from the switching time to the standby mode to the switching time to the active mode in the next X-ray computed tomography.

The power supply control unit 15 (to be described below) decides the switching time to the active mode and the switching time to the standby mode. The switching time to the active mode is, for example, 30 min before the start time of X-ray computed tomography. It is possible to switch from the standby mode to the active mode based on the time when the information of a patient in need of emergency care or diagnosis is input to at least one of the RIS 200, the HIS 201, and the console 11. In addition, when the information of a patient in need of emergency care or diagnosis is input to at least one of the RIS 200, the HIS 201, and the console 11, examination schedule data is updated. Note that the switching time to the active mode may be the time preceding the start time of X-ray computed tomography in the examination schedule data by a longer one of the second and third times.

The power supply control unit 15 controls the power supply unit 13 based on the examination schedule data stored in the storage unit 10 and the first and second times. More specifically, the power supply control unit 15 reads out examination schedule data on the day of X-ray computed tomography from the storage unit 10. The power supply control unit 15 decides the switching time to the standby mode which succeeds the end time of each X-ray computed tomography in the read examination schedule data by the first time. The power supply control unit 15 decides the switching time to the active mode which precedes the start time of each X-ray computed tomography in the read examination schedule data by the second time.

The power supply control unit 15 controls the power supply unit 13 to switch from the active mode to the standby mode in accordance with the switching time to the standby mode. The power supply control unit 15 controls the power supply unit 13 to switch from the standby mode to the active mode in accordance with the switching time to the active mode. Note that the power supply control unit 15 may decide, as the switching time to the active mode, the time preceding the start time of each X-ray computed tomography in the examination schedule data by a longer one of the second and third times.

(Mode Switching Function)

The mode switching function includes a function of switching from the standby mode to the active mode and a function of switching from the active mode to the standby mode. Processing (to be referred to as mode switching processing hereinafter) based on the mode switching function will be described below.

FIG. 2 is a flowchart showing a procedure for mode switching processing on the day of examination by X-ray computed tomography.

The X-ray computed tomography apparatus stores the examination schedule data received from the RIS 200 or the HIS 201 in the storage unit 10 on the day of examination by X-ray computed tomography (step Sa1). Note that examination schedule data to be stored in the storage unit 10 may be read out from a storage medium (not shown). The apparatus decides the switching time to the active mode which precedes the start time of each of a plurality of X-ray computed tomographies in the stored examination schedule data by the second time (step Sa2). Note that it is possible to decide, as the switching time to the active mode, the time preceding the start time of each of a plurality of X-ray computed tomographies by a longer one of the second and third times. The apparatus switches the mode of the power supply unit 13 from the standby mode to the active mode in accordance with the decided switching time to the active mode.

The apparatus supplies power to the bed unit 3, the high voltage generation unit 5, the gantry unit 7, and the console 11 in accordance with the active mode (step Sa3). At this time, the apparatus cancels the power saving state of the console 11. When power is supplied to the gantry unit 7, the first heater 711 heats the X-ray tube 71 up to the second threshold. When power is supplied to the gantry unit 7, the second heater 751 heats the X-ray detector 75 up to the third threshold. When power is supplied to the high voltage generation unit 5, the filament current generator of the high voltage generation unit 5 heats the cathode filament up to the first threshold.

When the start time of X-ray computed tomography arrives, the apparatus starts X-ray computed tomography (step Sa4). Upon completion of the X-ray computed tomography (step Sa5), the apparatus determines the presence/absence of the next X-ray computed tomography based on the stored examination schedule data before the lapse of the sum of the first and second times since the end time of the X-ray computed tomography (step Sa6). If there is the next X-ray computed tomography, the power supply unit 13 is kept in the active mode to repeat the processing from step Sa4 to step Sa6. If there is no next X-ray computed tomography, the cooling device 713 cools the X-ray tube 71 until the lapse of the first time since the end time of the X-ray computed tomography in step Sa5.

When the first time has elapsed since the end time of the X-ray computed tomography (step Sa7), the apparatus stops supplying power to the bed unit 3 and the gantry unit 7 (step Sa8). At this time, the console 11 is set in a power saving state. Note that at this time, the apparatus may stop supplying power to the high voltage generation unit 5. The apparatus repeats the processing from step Sa3 to step Sa8 until the number of times of execution of X-ray computed tomography coincides with the number of examination reservations included in the examination schedule data (step Sa9).

Figure 3:
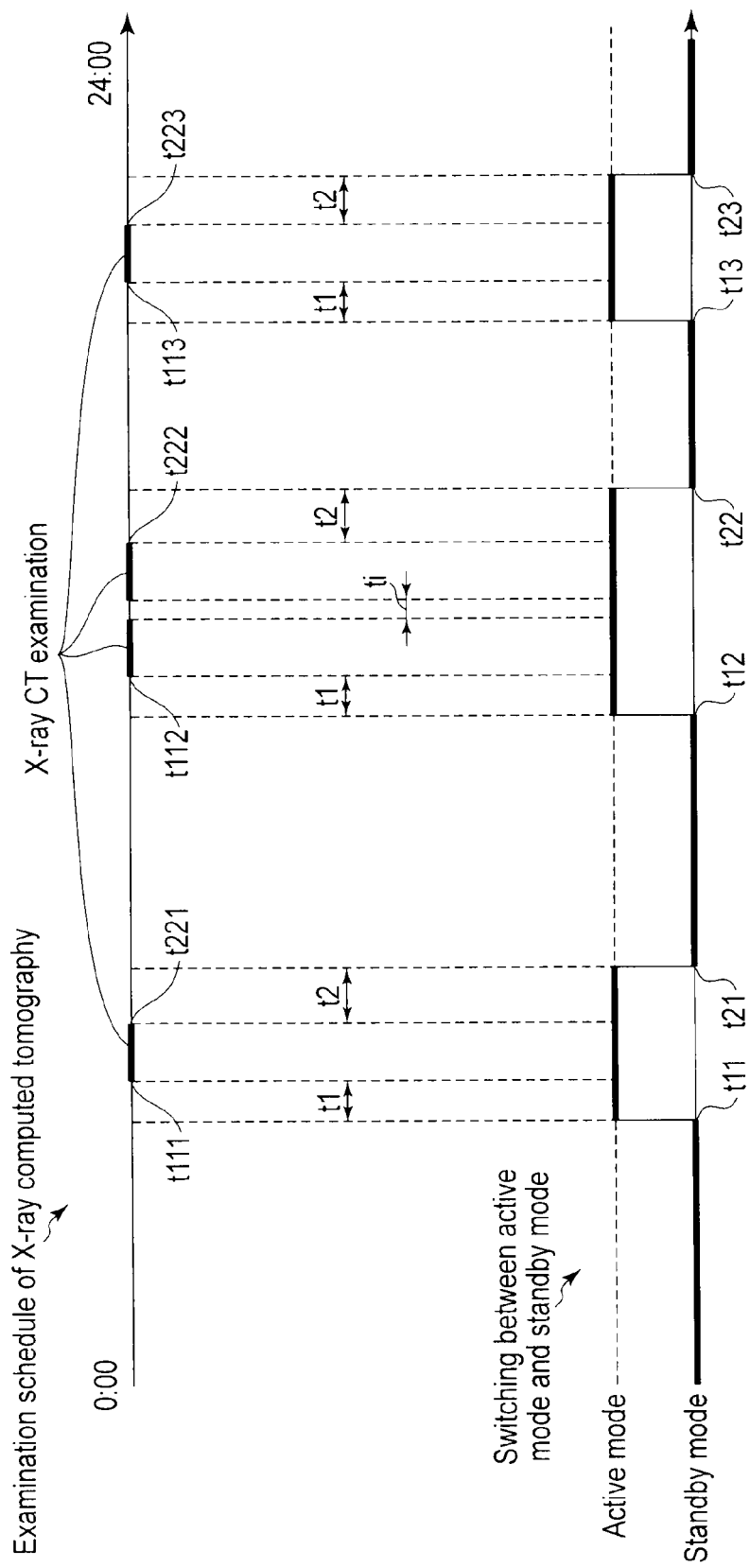
FIG. 3 is a view showing switching from the active mode to the standby mode and switching from the standby mode to the active mode, together with an examination schedule of X-ray computed tomography according to the first embodiment.

FIG. 3 is a view showing mode switching on the day of examination by X-ray computed tomography, together with an examination schedule of X-ray computed tomography. In the examination schedule in FIG. 3, the number of examination reservations is "4". Reference symbol t1 denotes the second time; and t2, the first time. In the time t1, the apparatus heats the X-ray tube 71 and X-ray detector 75 of the gantry unit 7. In the time t2, the apparatus cools the X-ray tube of the gantry unit 7. Reference symbols t111, t112, and t113 respectively denote the first, second, and fourth start times of X-ray computed tomography; t221, t222, and t223, the first, third, and fourth end times of X-ray computed tomography; and t11, t12, and t13, the switching times to the active mode. The times t11, t12, and t13 respectively correspond to the time preceding tl1 by t1, the time preceding t112 by t1, and the time preceding t113 by t1. Reference symbols t21, t22, and t23 respectively denote the switching times to the standby mode. The times t21, t22, and t23 respectively correspond to the time succeeding t221 by t2, the time succeeding t222 by t2, and the time succeeding t223 by t2. Reference symbol ti denotes the time interval between the end time of the second X-ray computed tomography and the start time of the third X-ray computed tomography.

Since t112 does not arrive before the lapse of (t1+t2) from t221, the apparatus executes the standby mode from t21 to t12. The start time of the third X-ray computed tomography arrives before the lapse of (t1+t2) from the end time of the second X-ray computed tomography (ti<t1+t2), and hence the apparatus does not execute the standby mode in the time interval between the end time of the second X-ray computed tomography and the start time of the third X-ray computed tomography. That is, the apparatus maintains the active mode in ti. The fourth X-ray computed tomography is the last X-ray computed tomography on the day. That is, the number of times (four) X-ray computed tomography has been executed coincides with the number (four) of examination reservations. The apparatus therefore switches the mode of the power supply unit 13 from the active mode to the standby mode at t23 when t2 has elapsed since t223.

The arrangement described above can obtain the following effects.

The X-ray computed tomography apparatus 1 according to this embodiment can switch from the active mode to the standby mode and from the standby mode to the active mode based on the examination schedule data received from at least one of the RIS 200 and the HIS 201. This makes it possible to set the X-ray computed tomography apparatus 1 in the active mode when it is used for examination, thereby efficiently using power. In addition, this can save the power consumed by the X-ray computed tomography apparatus. Furthermore, since mode switching is based on examination schedule data, no load is imposed on the operator.

(Second Embodiment)

FIG. 4 is a view showing the arrangement of an X-ray computed tomography apparatus according to the second embodiment. An X-ray computed tomography apparatus 1 according to the second embodiment includes a bed unit 3, a high voltage generation unit 5, a gantry unit 7, an interface 9, a storage unit 10, a console 11, a power supply unit 13, a power supply control unit 15, and a measurement unit 17.

The measurement unit 17 measures the temperature of an X-ray tube 71 and the temperature of an X-ray detector 75. The temperature of the X-ray tube 71 includes the temperature of the bearing portion (not shown) and the temperature of the cathode filament.

The storage unit 10 stores a correspondence table (to be referred to as the first correspondence table) among the time (to be referred to as the reconstruction time hereinafter) when a reconstruction unit 110 has reconstructed all images in examination by one X-ray computed tomography, the time (to be referred to as the storage time hereinafter) when all the images in examination by one X-ray computed tomography are transferred to at least one of the storage unit 10, a RIS 200, and a HIS 201, predetermined thresholds associated with temperature of the X-ray tube 71, the time (to be referred to as the first arrival time hereinafter) taken for the temperature of the X-ray tube 71 to arrive at the second threshold from a temperature lower than the second threshold, and the temperature of the X-ray tube 71, and a correspondence table (to be referred to as the second correspondence table) between the time (to be referred to as the second arrival time hereinafter) taken for the temperature of the X-ray detector 75 to arrive at the third threshold from a temperature lower than the third threshold and the temperature of the X-ray detector 75. Note that the storage unit 10 may store a correspondence table (to be referred to as the third correspondence table) between the time (to be referred to as the third arrival time hereinafter) taken for the temperature of the cathode filament to arrive at the first threshold from a temperature lower than the first threshold and the temperature of the cathode filament.

The power supply control unit 15 decides the time (to be referred to as the arrival time hereinafter) when the measured temperature of the X-ray tube 71 arrives at a predetermined threshold from a temperature lower than the predetermined threshold. The power supply control unit 15 decides the latest time among the arrival time, the reconstruction time, and the storage time as the switching time to the standby mode. The power supply control unit 15 decides the first arrival time based on the measured temperature of the X-ray tube 71 and the first correspondence table. The power supply control unit 15 decides the second arrival time based on the measured temperature of the X-ray detector 75 and the second correspondence table. The power supply control unit 15 selects a longer one of the first and second arrival times. The power supply control unit 15 decides, as the switching time to the active mode, the time preceding the start time of each of a plurality of X-ray computed tomographies in examination schedule data by the selected time. Note that the power supply control unit 15 may decide the switching time to the active mode in consideration of also the third arrival time.

More specifically, the power supply control unit 15 decides the third arrival time based on the measured temperature of the cathode filament of the X-ray tube 71 and the third correspondence table. The power supply control unit 15 selects the longest time among the decided third arrival time, first time, and second time. The power supply control unit 15 decides, as the switching time to the active mode, the time preceding the start time of each of a plurality of X-ray computed tomographies in the examination schedule data by the selected time.

The power supply control unit 15 controls the power supply unit 13 to switch from the active mode to the standby mode in accordance with the switching time to the standby mode. The power supply control unit 15 controls the power supply unit 13 to switch from the standby mode to the active mode in accordance with the switching time to the active mode.

(Mode Switching Function)

Figure 5:
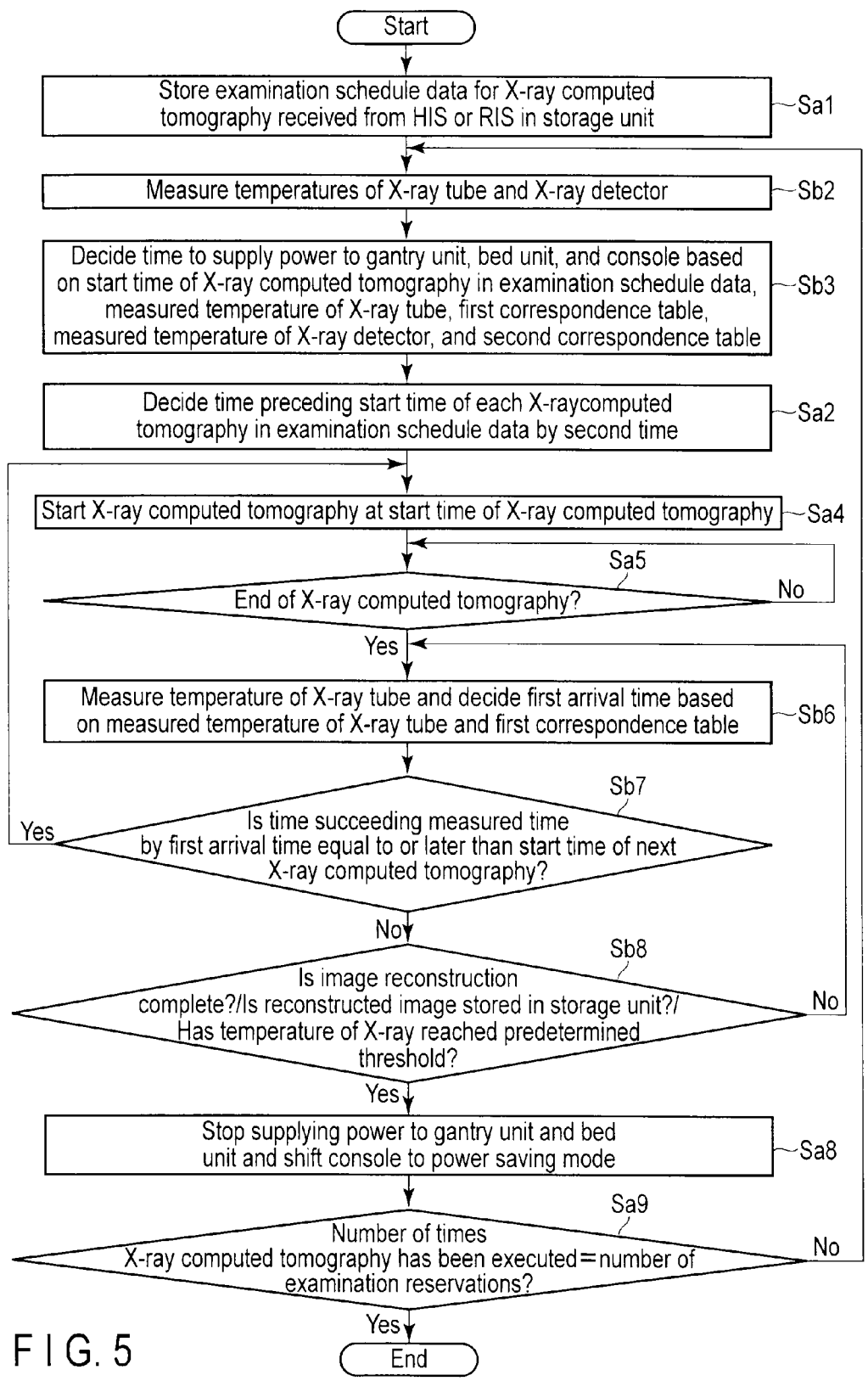
FIG. 5 is a flowchart showing a processing procedure for switching from the active state to the standby mode based on the state of an X-ray computed tomography apparatus and for switching from the standby mode to the active mode based on the state of the X-ray computed tomography apparatus and examination schedule data according to the second embodiment.

FIG. 5 is a flowchart showing a procedure for mode switching processing on the day of examination by X-ray computed tomography.

The X-ray computed tomography apparatus stores the examination schedule data received from the RIS 200 or the HIS 201 in the storage unit 10 on the day of examination by X-ray computed tomography (step Sa1). Note that examination schedule data to be stored in the storage unit 10 may be read out from a storage medium (not shown).

The apparatus measures the temperatures of the X-ray tube 71 and X-ray detector 75 (step Sb2). The apparatus decides the first arrival time based on the temperature of the X-ray tube 71 and the first correspondence table. The apparatus decides the second arrival time based on the temperature of the X-ray detector 75 and the second correspondence table. The apparatus selects a longer one of the first and second arrival times. The apparatus decides the time (the switching time to the active mode) preceding the start time of X-ray computed tomography by the selected time (step Sb3). Note that it is possible to include the time taken to heat the cathode filament in step Sb3. At this time, the apparatus decides the third arrival time based on the measured temperature of the X-ray tube and the third correspondence table. The apparatus then selects the longest time among the first arrival time, the second arrival time, and the third arrival time. The apparatus decides, as the switching time to the active mode, the time preceding the start time of X-ray computed tomography by the selected time. Following step Sb3, the apparatus executes the processing from step Sa3 to step Sa5. After step Sa5, the X-ray tube 71 is cooled. At this time, the temperature of the X-ray tube 71 is measured.

The apparatus decides the first arrival time based on the temperature of the X-ray tube 71 and the first correspondence table (step Sb6). If the time succeeding the time (to be referred to as the measurement time hereinafter) when the temperature of the X-ray tube 71 has been measured, by the first arrival time, becomes equal to the start time of the next X-ray computed tomography, the apparatus stops cooling the X-ray tube 71. After stopping cooling, the apparatus heats the X-ray tube 71 until the temperature of the X-ray tube 71 reaches the second threshold (first arrival time). The end time of heating of the X-ray tube 71 becomes the start time of the next X-ray computed tomography, and the apparatus repeats the processing from step Sa4 to step Sb7 while maintaining the power supply unit 13 in the active mode (step Sb7). Note that, in steps Sb6 and Sb7, it is possible to include the time during which the cathode filament is heated. At this time, the apparatus decides the third arrival time based on the measured temperature of the X-ray tube and the third correspondence table. The apparatus then selects a longer one of the first and third arrival times. The apparatus executes the processing in step Sb7 by using the time succeeding the measurement time by the selected time.

If the time succeeding the measurement time by the first arrival time is not equal to the start time of the next X-ray computed tomography, the apparatus cools the X-ray tube 71 to a predetermined threshold, reconstructs an image captured by the X-ray computed tomography, and determines whether the reconstructed image is transferred to and stored in the storage unit 10 (step Sb8).

Assume that one of the following conditions does not hold: the X-ray tube 71 is cooled to a predetermined threshold, an image captured by the X-ray computed tomography is reconstructed, and the reconstructed image is transferred to and stored in the storage unit 10. In this case, the apparatus repeats the processing in steps Sb6 and Sb7. Assume that all the following conditions hold: the X-ray tube 71 is cooled to the predetermined threshold, an image captured by the X-ray computed tomography is reconstructed, and the reconstructed image is transferred to and stored in the storage unit 10. In this case, the apparatus executes the processing in steps Sa8 and Sa9. The apparatus repeats the processing from step Sb2 to step Sa9 until the number of times of execution of X-ray computed tomography becomes equal to the number of examination reservations included in the examination schedule data (step Sa9). Note that the reconstructed image may be transferred to and stored in an image observation device (not shown) or an image storage device (not shown).

Figure 6:
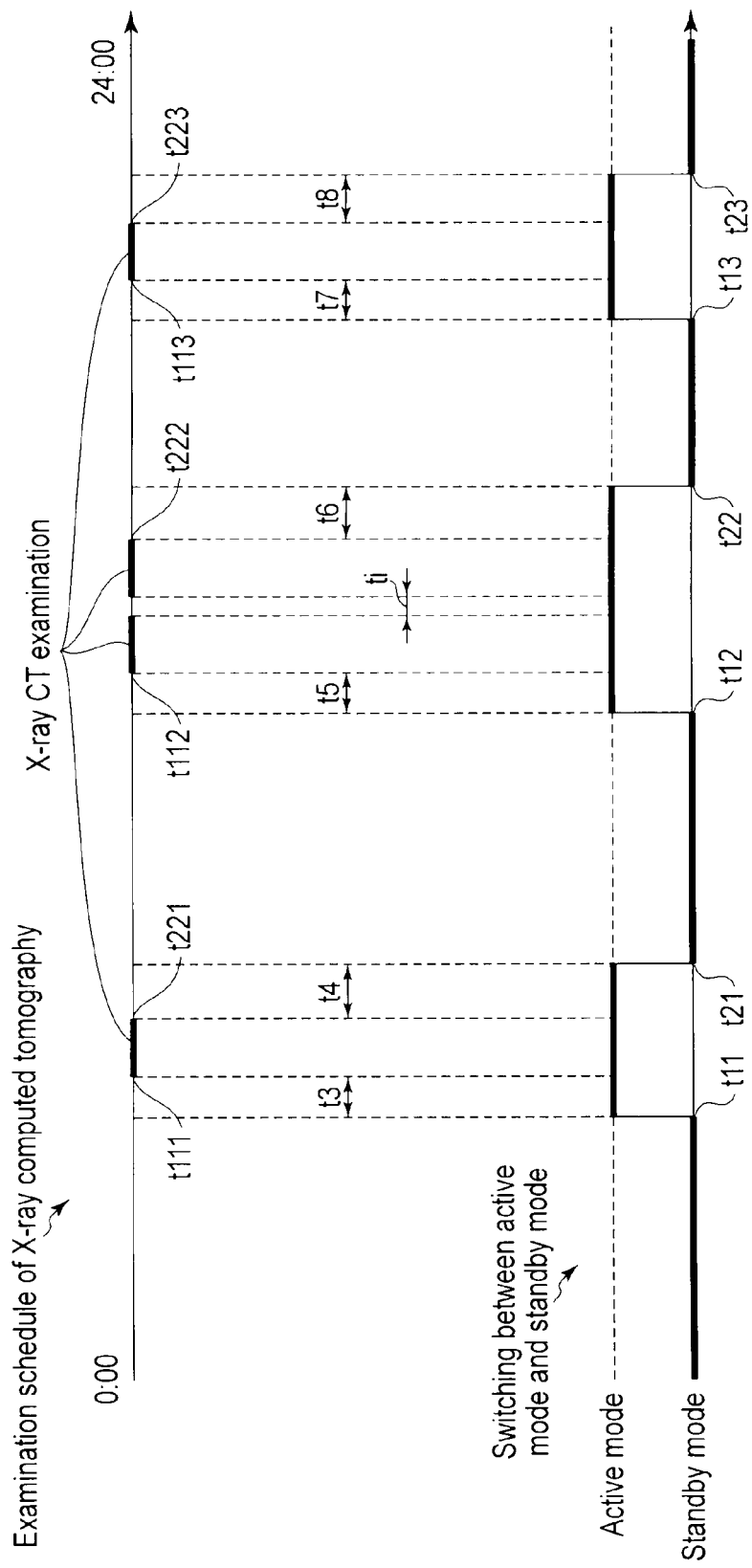
FIG. 6 is a view showing switching from the active mode to the standby mode and switching from the standby mode to the active mode, together with an examination schedule of X-ray computed tomography according to the second embodiment.
Figure 7:
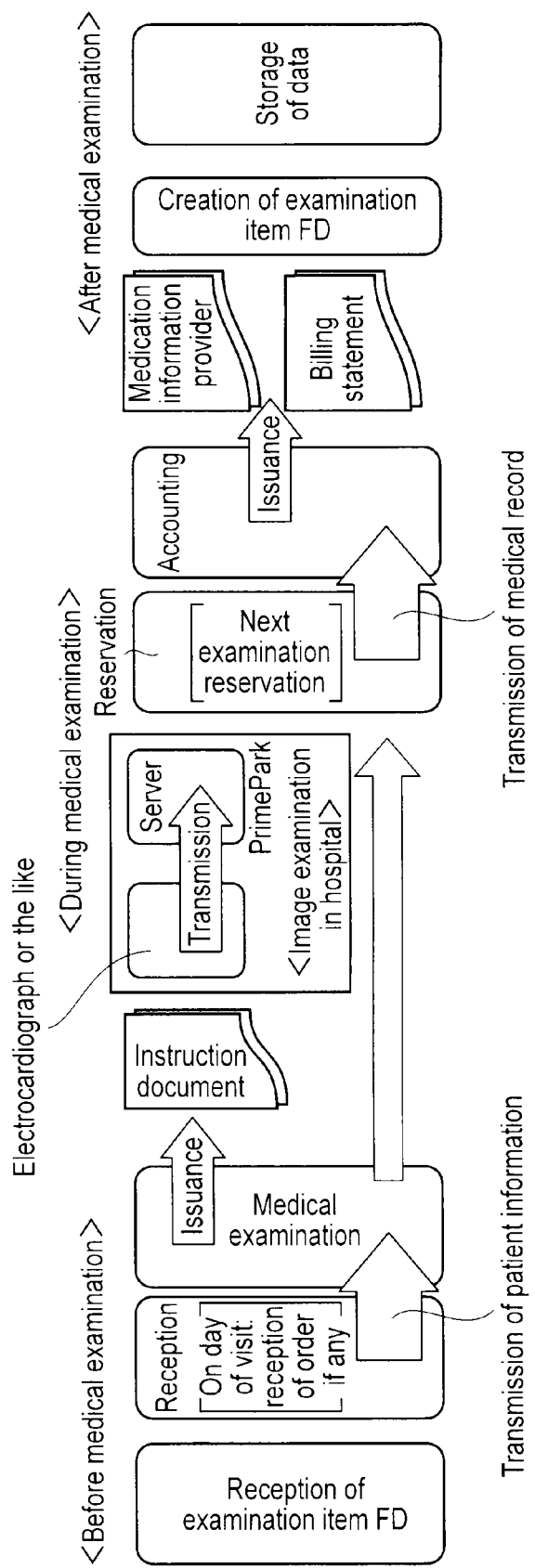
FIG. 7 is a view showing a conventional general examination procedure.

FIG. 6 is a view showing mode switching on the day of examination by X-ray computed tomography, together with an examination schedule of X-ray computed tomography. In the examination schedule in FIG. 6, the number of examination reservations is "4". Reference symbols t3, t5, and t7 each denote a longer one of the first and second arrival times. More specifically, reference symbols t3, t5, and t7 each denote the time including the time during which the X-ray tube 71 is heated and the third arrival time during which the X-ray detector 75 is heated. Note that the times t3, t5, and t7 each may include the time during which the cathode filament is heated. For each of the times t3, t5, and t7, the gantry unit 7 is heated. Reference symbols t4, t6, and t8 each denote the time including the time during which the X-ray tube 71 is cooled to a predetermined threshold, the time during which an image is reconstructed, and the time during which the reconstructed image is transferred to and stored in the storage unit 10, after a corresponding one of the first, third, and fourth X-ray computed tomographies. For each of the times t4, t6, and t8, the gantry unit 7 is cooled.

Reference symbols t111, t112, and t113 respectively denote the start times of the first, second, and fourth X-ray computed tomographies; t221, t222, and t223, the end times of the first, third, and fourth X-ray computed tomographies; and t11, t12, and t13, the switching times to the active mode. The times t11, t12, and t13 respectively correspond to the time preceding t111 by t3, the time preceding t112 by t5, and the time preceding t113 by t7. Reference symbols t21, t22, and t23 respectively denote the switching times to the standby mode. The times t21, t22, and t23 respectively correspond to the time succeeding t221 by t4, the time succeeding t222 by t6, and the time succeeding t223 by t8. Reference symbol ti denotes the time interval between the end time of the second X-ray computed tomography and the start time of the third X-ray computed tomography.

The apparatus measures the temperature of the X-ray tube 71 with time after t221. The apparatus decides the first arrival time for each measurement time based on the measured temperature of the X-ray tube 71 and the first correspondence table. The time succeeding the measurement time by the first arrival time does not become equal to the start time of the second X-ray computed tomography at any measurement time from t221 to t21. For this reason, the apparatus switches the mode of the power supply unit 13 from the active mode to the standby mode at the time succeeding t221 by t4.

The apparatus measures the temperature of X-ray tube 71 with time in ti. The apparatus decides the first arrival time for each measurement time based on the measured temperature of the X-ray tube 71 and the first correspondence table. The time succeeding the measurement time by the first arrival time coincides with the start time of the third X-ray computed tomography at either measurement time until the lapse of ti since the end time of the second X-ray computed tomography. For this reason, the apparatus does not switch the mode of the power supply unit 13 from the active mode to the standby mode. That is, the apparatus executes the third X-ray computed tomography while maintaining the power supply unit 13 in the active mode.

The apparatus measures the temperature of the X-ray tube 71 with time after t222. The apparatus decides the first arrival time for each measurement time based on the measured temperature of the X-ray tube 71 and the first correspondence table. The time succeeding the measurement time by the first arrival time does not coincide with the start time of the fourth X-ray computed tomography at any measurement time from t222 to t22. For this reason, the apparatus switches the mode of the power supply unit 13 from the active mode to the standby mode at the time succeeding t222 by t6.

The fourth X-ray computed tomography is the last X-ray computed tomography on the day. That is, the number of times (four) X-ray computed tomography has been executed becomes equal to the number (four) of examination reservations. Therefore, the apparatus switches the mode of the power supply unit 13 from the active mode to the standby mode at t23 succeeding t223 by t2.

The arrangement described above can obtain the following effects.

The X-ray computed tomography apparatus 1 according to this embodiment can switch from the active mode to the standby mode and from the standby mode to the active mode based on the examination schedule data received from at least one of the RIS 200 and the HIS 201 and the state of the apparatus (the temperature of the X-ray tube 71, the temperature of the X-ray detector 75, the time when image reconstruction is complete, and the time when the image is stored and transferred). This makes it possible to set the X-ray computed tomography apparatus 1 in the active mode when it is used for examination, thereby efficiently using power. In addition, this can save the power consumed by the X-ray computed tomography apparatus 1. Furthermore, since mode switching is based on examination schedule data, no load is imposed on the operator. Monitoring the state of the X-ray computed tomography apparatus 1 in real time can implement fine mode switching operation and further save power.

According to a modification of the above embodiment, when implementing the technical idea of the X-ray computed tomography apparatus 1 by using an X-ray diagnostic apparatus, the apparatus includes the same constituent elements as those of the arrangement shown in, for example, FIG. 1 or 4 except for the rotating ring 73 and the like. In this case, for example, each process in the mode switching function corresponding to FIGS. 2 and 5 is implemented by substituting the X-ray computed tomography apparatus by the X-ray diagnostic apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising a gantry unit including an X-ray tube configured to generate X-rays and an X-ray detector configured to detect X-rays transmitted through an object, a bed unit on which the object is placed, and a console configured to control the gantry unit and the bed unit for X-ray computed tomography, and to reconstruct an image based on projection data acquired by the X-ray computed tomography, the apparatus comprising:
    a storage unit configured to store examination schedule data of the X-ray computed tomography;
    a power supply unit configured to selectively operate between an active mode of supplying power to at least one of the gantry unit, the bed unit, and the console, and a standby mode of stopping supplying power to at least one of the bed unit and the gantry unit and supplying, to the console, a non-zero power smaller than power supplied in the active mode; and
    a power supply control unit configured to control switching from the active mode to the standby mode based on the examination schedule data.

2. The apparatus according to claim 1, further comprising an interface configured to connect to, via an electronic communication line, at least one of a radiology information system and a hospital information system, which are configured to input or store the examination schedule data,
    wherein the storage unit further stores the examination schedule data received from the radiology information system or the hospital information system via the interface.

3. The apparatus according to claim 1, wherein the storage unit further stores a cooling time from an end time of X-ray computed tomography to a time when a temperature state of the X-ray tube reaches a cooled state, and
    the power supply control unit controls switching from the active mode to the standby mode based on the examination schedule data and the cooling time.

4. The apparatus according to claim 1, wherein the power supply control unit further controls switching from the standby mode to the active mode based on the examination schedule data.

5. The apparatus according to claim 1, wherein the storage unit further stores a heating time in which a temperature state of the X-ray detector reaches a heated state from a cooled state, and
    the power supply control unit further controls switching from the standby mode to the active mode based on the examination schedule data and the heating time.

6. An X-ray computed tomography apparatus comprising a gantry unit including an X-ray tube configured to generate X-rays and an X-ray detector configured to detect X-rays transmitted through an object, a bed unit on which the object is placed, and a console configured to control the gantry unit and the bed unit for X-ray computed tomography, and to reconstruct an image based on projection data acquired by the X-ray computed tomography, the apparatus comprising:
    a power supply unit configured to selectively operate between an active mode of supplying power to at least one of the gantry unit, the bed unit, and the console, and a standby mode of stopping supplying power to at least one of the bed unit and the gantry unit and supplying, to the console, a non-zero power smaller than power supplied in the active mode; and
    a power supply control unit configured to control switching from the active mode to the standby mode based on a temperature state of the gantry unit and a processed state of the projection data in the console.

7. The apparatus according to claim 6, further comprising:
    a measurement unit configured to measure a temperature of the X-ray tube and a temperature of the X-ray detector; and
    a storage unit configured to store an image reconstructed by the console and a predetermined threshold,
    wherein the temperature state of the gantry unit is a cooled state in which the measured temperature of the X-ray tube reaches the predetermined threshold from a temperature higher than the predetermined threshold, and
    the processed state of the projection data in the console is a state in which the image is reconstructed and stored in the storage unit.

8. The apparatus according to claim 6, further comprising:
    an interface configured to connect to at least one of a radiology information system and a hospital information system, which are configured to input or store the examination schedule data via an electronic communication line;
    a storage unit configured to store the examination schedule data received from the radiology information system or the hospital information system via the interface; and
    a measurement unit configured to measure a temperature of the X-ray tube and a temperature of the X-ray detector,
    wherein the power supply control unit further controls switching from the standby mode to the active mode based on at least one of the measured temperature of the X-ray tube and the measured temperature of the X-ray detector and the examination schedule data.

9. An X-ray computed tomography apparatus comprising a gantry unit including an X-ray tube configured to generate X-rays and an X-ray detector configured to detect X-rays transmitted through an object, a bed unit on which the object is placed, and a console configured to control the gantry unit and the bed unit for X-ray computed tomography, and to reconstruct an image based on projection data acquired by the X-ray computed tomography, the apparatus comprising:
    a storage unit configured to store examination schedule data of the X-ray computed tomography;
    a power supply unit configured to selectively operate between an active mode of supplying power to at least one of the gantry unit, the bed unit, and the console, and a standby mode of stopping supplying power to at least one of the bed unit and the gantry unit and supplying, to the console, a non-zero power smaller than power supplied in the active mode; and a power supply control unit configured to control switching from the active mode to the standby mode based on a temperature state of the gantry unit and a processed state of the projection data in the console, and to control switching from the standby mode to the active mode based on the temperature state of the gantry unit and the examination schedule data.

10. The apparatus according to claim 9, further comprising an interface configured to connect to at least one of a radiology information system and a hospital information system, which are configured to input or store the examination schedule data via an electronic communication line, wherein the storage unit further stores the examination schedule data received from the radiology information system or the hospital information system via the interface.

11. An X-ray diagnostic apparatus comprising a gantry unit including an X-ray tube configured to generate X-rays and an X-ray detector configured to detect X-rays transmitted through an object, a bed unit on which the object is placed, and a console configured to control the gantry unit and the bed unit for X-ray diagnostic imaging, and to generate an image based on projection data acquired by the X-ray diagnostic imaging, the apparatus comprising:

a storage unit configured to store examination schedule data of the X-ray diagnostic imaging;

a power supply unit configured to selectively operate between an active mode of supplying power to at least one of the gantry unit, the bed unit, and the console, and a standby mode of stopping supplying power to at least one of the bed unit and the gantry unit and supplying, to the console, a non-zero power smaller than power supplied in the active mode; and a power supply control unit configured to control switching from the active mode to the standby mode based on the examination schedule data.

* * * * *